US012345628B2

United States Patent
Morita et al.

(10) Patent No.: US 12,345,628 B2
(45) Date of Patent: Jul. 1, 2025

(54) OPTICAL MEASUREMENT DEVICE AND OPTICAL MEASUREMENT METHOD

(71) Applicants: SEKISUI MEDICAL CO., LTD., Tokyo (JP); HAMAMATSU PHOTONICS K.K., Hamamatsu (JP)

(72) Inventors: Motoki Morita, Tokyo (JP); Keigo Kohno, Tokyo (JP); Daichi Susuki, Hamamatsu (JP); Fusanori Kondo, Hamamatsu (JP)

(73) Assignees: SEKISUI MEDICAL CO., LTD., Tokyo (JP); HAMAMATSU PHOTONICS K.K., Hamamatsu (JP)

( * ) Notice: Subject to any disclaimer, the term of this patent is extended or adjusted under 35 U.S.C. 154(b) by 89 days.

(21) Appl. No.: 17/912,578

(22) PCT Filed: Mar. 23, 2021

(86) PCT No.: PCT/JP2021/012057
§ 371 (c)(1),
(2) Date: Sep. 19, 2022

(87) PCT Pub. No.: WO2021/193660
PCT Pub. Date: Sep. 30, 2021

(65) Prior Publication Data
US 2023/0136517 A1    May 4, 2023

(30) Foreign Application Priority Data
Mar. 24, 2020   (JP) .................................. 2020-052380

(51) Int. Cl.
*G01N 21/27*    (2006.01)
*G01N 21/25*    (2006.01)
*G01N 21/47*    (2006.01)

(52) U.S. Cl.
CPC .......... *G01N 21/27* (2013.01); *G01N 21/255* (2013.01); *G01N 2021/478* (2013.01)

(58) Field of Classification Search
CPC ................. G01N 21/27; G01N 21/255; G01N 2021/478; G01N 33/4875; G01N 21/8483; G01N 21/78
See application file for complete search history.

(56) References Cited

U.S. PATENT DOCUMENTS

2008/0064119 A1*   3/2008   Panotopoulos .. G01N 33/54388
                                                                 436/514
2009/0180929 A1*   7/2009   Petruno ............ G01N 33/54388
                                                                 422/400

(Continued)

FOREIGN PATENT DOCUMENTS

EP          3361238 A1     8/2018
JP       2008-170187 A     7/2008

(Continued)

OTHER PUBLICATIONS

International Preliminary Report on Patentability mailed Oct. 6, 2022 for PCT/JP2021/012057.

*Primary Examiner* — Tarifur R Chowdhury
*Assistant Examiner* — Kemaya Nguyen
(74) *Attorney, Agent, or Firm* — Faegre Drinker Biddle & Reath LLP (57) ABSTRACT

An optical measurement device 1 includes: a measurement unit; and a determination unit, wherein the determination unit calculates a difference value between the initial measurement value and the latter measurement value when the measurement value exceeds the first threshold value after the sample is held by the lateral flow test strip, determines that the sample is positive when the difference value exceeds a second threshold value set in advance, and determines that (Continued)

the sample is negative when the difference value is the second threshold value or less.

6 Claims, 7 Drawing Sheets

(56) References Cited

U.S. PATENT DOCUMENTS

| | | | | |
|---|---|---|---|---|
| 2012/0083044 | A1* | 4/2012 | Sturman | G01N 33/689 |
| | | | | 422/402 |
| 2013/0065321 | A1* | 3/2013 | Nazareth | G01N 21/8483 |
| | | | | 422/69 |
| 2014/0271362 | A1 | 9/2014 | Markovsky et al. | |
| 2015/0241455 | A1* | 8/2015 | Parsons | G01N 21/6428 |
| | | | | 422/68.1 |
| 2018/0095035 | A1* | 4/2018 | Wu | G01N 21/47 |
| 2018/0299385 | A1* | 10/2018 | Honda | G01N 33/54366 |

FOREIGN PATENT DOCUMENTS

| | | |
|---|---|---|
| JP | 2009-133813 A | 6/2009 |
| JP | 2011-174865 A | 9/2011 |
| WO | WO-2009/145250 A1 | 12/2009 |
| WO | WO-2010/058472 A1 | 5/2010 |
| WO | WO-2017/061494 A1 | 4/2017 |
| WO | WO-2019/006500 A1 | 1/2019 |

* cited by examiner

OPTICAL MEASUREMENT DEVICE AND OPTICAL MEASUREMENT METHOD

TECHNICAL FIELD

The present disclosure relates to an optical measurement device and an optical measurement method.

BACKGROUND ART

As a method of detecting a measurement target substance in a sample, a lateral flow membrane assay is known. The lateral flow membrane assay is a method of detecting a measurement target substance in a sample by using a test strip (lateral flow test strip) including a labeling substance holding unit which holds a labeling substance binding to the measurement target substance to be eluted and a detection area which fixes a substance binding to the measurement target substance. Examples of lateral flow membrane assays include immunochromatography and nucleic acid chromatography. When the measurement target substance in the sample binds to the labeling substance to form a complex and the complex develops to the detection area, the complex is trapped by a binding substance fixed in a band shape and a signal from the labeling substance is generated on a test line. Thus, it is possible to qualitatively or quantitatively analyze the measurement target substance in the sample by optically measuring a signal on the test line in the lateral flow test strip using an optical measurement device.

As the optical measurement device used in the lateral flow membrane assay, for example, optical measurement devices described in Patent Literatures 1 and 2 are known. These conventional optical measurement devices include a loading unit which loads a plurality of lateral flow test strips, a reading unit which reads a coloration state of the lateral flow test strip loaded in the loading unit, and a control unit which performs an inspection process on the basis of the coloration state of the lateral flow test strip read by the reading unit.

CITATION LIST

Patent Literature

Patent Literature 1: Japanese Unexamined Patent Publication No. 2009-133813
Patent Literature 2: International Publication WO2010/58472

SUMMARY OF INVENTION

Technical Problem

However, in the inspection using the above-described optical measurement device, the adhesion of a foreign substance to the lateral flow test strip becomes a problem. As such a foreign substance, for example, powder of a constituent substance or the like of the lateral flow test strip is assumed. When visually checking the coloration state of the test line, the foreign substance rarely affects the determination. On the other hand, when the coloration state of the test line is optically read by using the lateral flow test strip to which the foreign substance adheres, it is conceivable that a measurement value exceeds a threshold value caused by the adhesion of the foreign substance and an originally negative sample is determined as positive.

The present disclosure has been made to solve the above-described problems and an object thereof is to provide an optical measurement device and an optical measurement method capable of ensuring sample determination accuracy even when a foreign substance adheres to a lateral flow test strip.

Solution to Problem

An optical measurement device according to an aspect of the present disclosure includes: a measurement unit which emits measurement light to a detection area of a lateral flow test strip and measures light obtained from the detection area by the emission of the measurement light for a predetermined period; and a determination unit which determines whether or not a sample held in the lateral flow test strip is negative or positive on the basis of a comparison between a measurement value obtained by the measurement unit and a first threshold value set in advance, wherein the determination unit calculates a difference value between an initial measurement value and a latter measurement value when the measurement value exceeds the first threshold value after the sample is held by the lateral flow test strip, determines that the sample is positive when the difference value exceeds a second threshold value set in advance, and determines that the sample is negative when the difference value is the second threshold value or less.

In this optical measurement device, it is determined whether or not the sample held by the lateral flow test strip is negative or positive on the basis of the comparison between the measurement value of the light obtained from the detection area by the emission of the measurement light and the first threshold value set in advance. When the sample is positive, the measurement value gradually increases as the measurement period elapses and exceeds the first threshold value. When the sample is negative, the measurement value does not increase as the measurement period elapses and becomes the first threshold value or less. On the other hand, when the foreign substance adheres to the detection area of the lateral flow test strip, the measurement value caused by the adhesion of the foreign substance tends to have a constant value over the entire measurement period. Therefore, it is conceivable that an originally negative sample is determined positive when the measurement value caused by the adhesion of the foreign substance exceeds the first threshold value. On the other hand, in this optical measurement device, the difference value between the initial measurement value and the latter measurement value is calculated when the measurement value exceeds the first threshold value. It is possible to distinguish whether or not the measurement value exceeding the first threshold value is caused by the adhesion of the foreign substance by comparing this difference value with the second threshold value. Thus, it is possible to ensure the sample determination accuracy even when the foreign substance adheres to the lateral flow test strip.

The first threshold value may be set to gradually decrease as a measurement period elapses, and the determination unit may calculate the difference value when the measurement value exceeds the first threshold value and the initial measurement value exceeds the first threshold value at the latter measurement. It is possible to improve the sample determination accuracy by setting the first threshold value to gradually decrease as the measurement period elapses. Further, it is possible to accurately distinguish whether or not the measurement value exceeding the first threshold value is caused by the adhesion of the foreign substance even when the first threshold value is set to gradually decrease as the measurement period elapses by comparing the initial measurement value with the first threshold value at the latter measurement.

The determination unit may calculate the difference value when the measurement value exceeds the first threshold value at a reaction completion time point of the lateral flow test strip. The reaction completion time point is, for example, a time point at which a predetermined time for determining negative elapses. It is possible to more accurately distinguish whether or not the measurement value exceeding the first threshold value is caused by the adhesion of the foreign substance by calculating the difference value when the measurement value exceeds the first threshold value after the reaction of the lateral flow test strip is completed.

An optical measurement method according to an aspect of the present disclosure includes: a measurement step of emitting measurement light to a detection area of a lateral flow test strip and measuring light obtained from the detection area by the emission of the measurement light for a predetermined period; and a determination step of determining whether or not a sample held by the lateral flow test strip is negative or positive on the basis of a comparison between a measurement value obtained by the measurement step and a first threshold value set in advance, wherein the determination step calculates a difference value between the initial measurement value and the latter measurement value when the measurement value exceeds the first threshold value after the sample is held by the lateral flow test strip, determines that the sample is positive when the difference value exceeds a second threshold value set in advance, and determines that the sample is negative when the difference value is the second threshold value or less.

In this optical measurement method, the difference value between the initial measurement value and the measurement value at the latter measurement is calculated when the measurement value exceeds the first threshold value. It is possible to distinguish whether or not the measurement value exceeding the first threshold value is caused by the adhesion of the foreign substance by comparing this difference value with the second threshold value. Thus, it is possible to ensure the sample determination accuracy even when the foreign substance adheres to the lateral flow test strip.

The first threshold value may be set to gradually decrease as a measurement period elapses, and the determination step may calculate the difference value when the measurement value exceeds the first threshold value and the initial measurement value exceeds the first threshold value at the latter measurement. It is possible to improve the sample determination accuracy by setting the first threshold value to gradually decrease as the measurement period elapses. Further, it is possible to accurately distinguish whether or not the measurement value exceeding the first threshold value is caused by the adhesion of the foreign substance even when the first threshold value is set to gradually decrease as the measurement period elapses by comparing the initial measurement value with the first threshold value at the latter measurement.

The determination step may calculate the difference value when the measurement value exceeds the first threshold value at a reaction completion time point of the lateral flow test strip. It is possible to more accurately distinguish whether or not the measurement value exceeding the first threshold value is caused by the adhesion of the foreign substance by calculating the difference value when the measurement value exceeds the first threshold value after the reaction of the lateral flow test strip is completed.

Advantageous Effects of Invention

According to the present disclosure, it is possible to ensure sample determination accuracy even when a foreign substance adheres to a lateral flow test strip.

DESCRIPTION OF EMBODIMENTS

Hereinafter, a preferred embodiment of an optical measurement device and an optical measurement method according to an aspect of the present invention will be described in detail with reference to the drawings.

Figure 1:
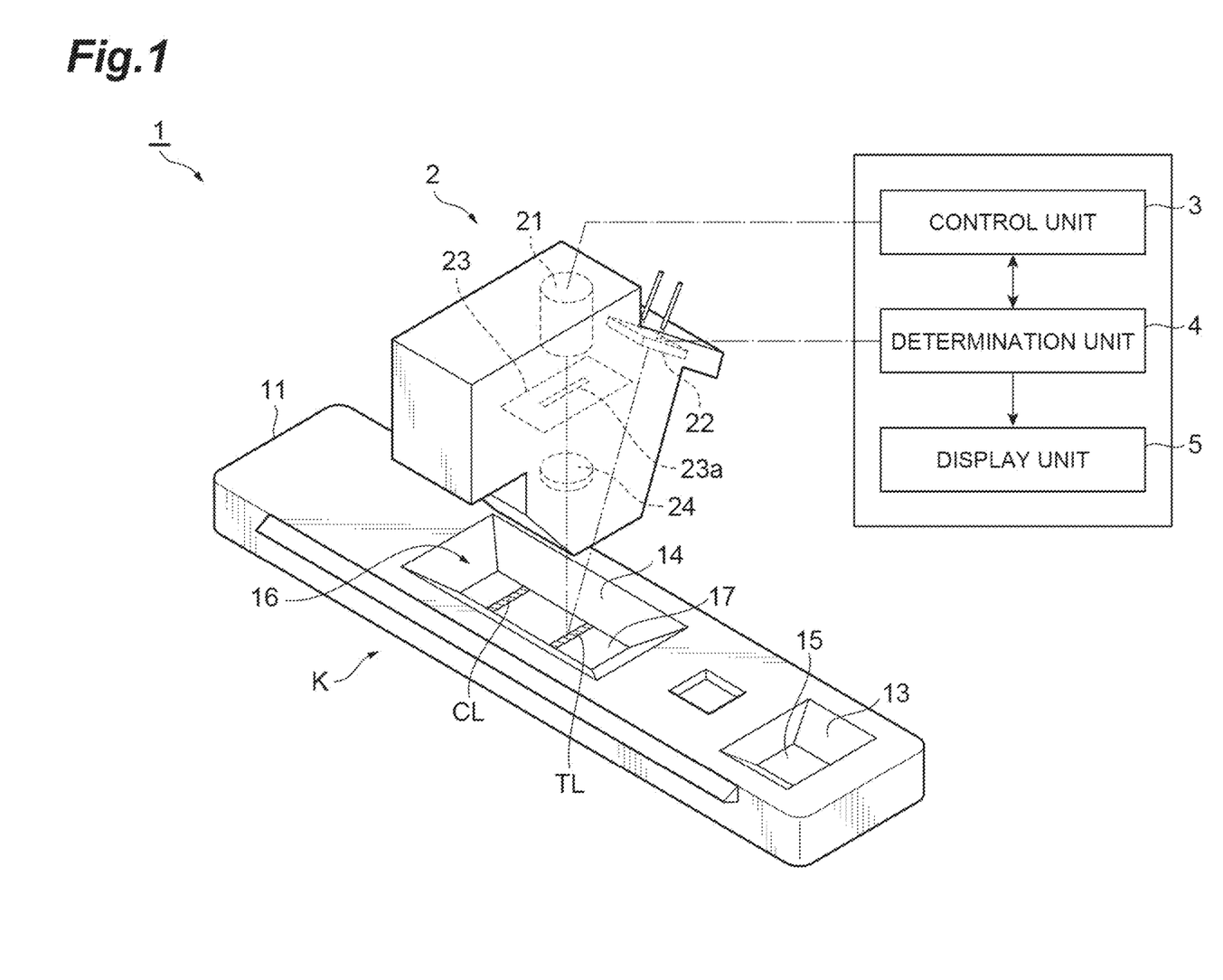
FIG. 1 is a perspective view showing an embodiment of an optical measurement device.

FIG. 1 is a diagram showing an embodiment of the optical measurement device. An optical measurement device 1 shown in the same drawing is a device which determines the reactivity of an antibody-antigen reaction or the like in a sample dropped on a lateral flow test strip K by measuring the coloration of a test line TL of the lateral flow test strip K.

As shown in FIG. 1, the optical measurement device 1 includes an optical head (measurement unit) 2 which emits measurement light and measures reflection light, a placement plate which places the lateral flow test strip K thereon, and a drive mechanism (not shown) which relatively moves the placement plate with respect to the optical head 2. Further, the optical measurement device 1 includes a control unit (measurement unit) 3 which controls the optical head 2, a determination unit 4 which makes a determination on the lateral flow test strip K on the basis of the measurement result of the reflection light, and a display unit 5 which displays a determination result of the determination unit 4 as functional elements. These functional elements are realized by, for example, a computer system including a storage device such as a CPU, a RAM, and a ROM, an input device such as a keyboard and a mouse, and an auxiliary storage device such as a hard disk.

Figure 2:
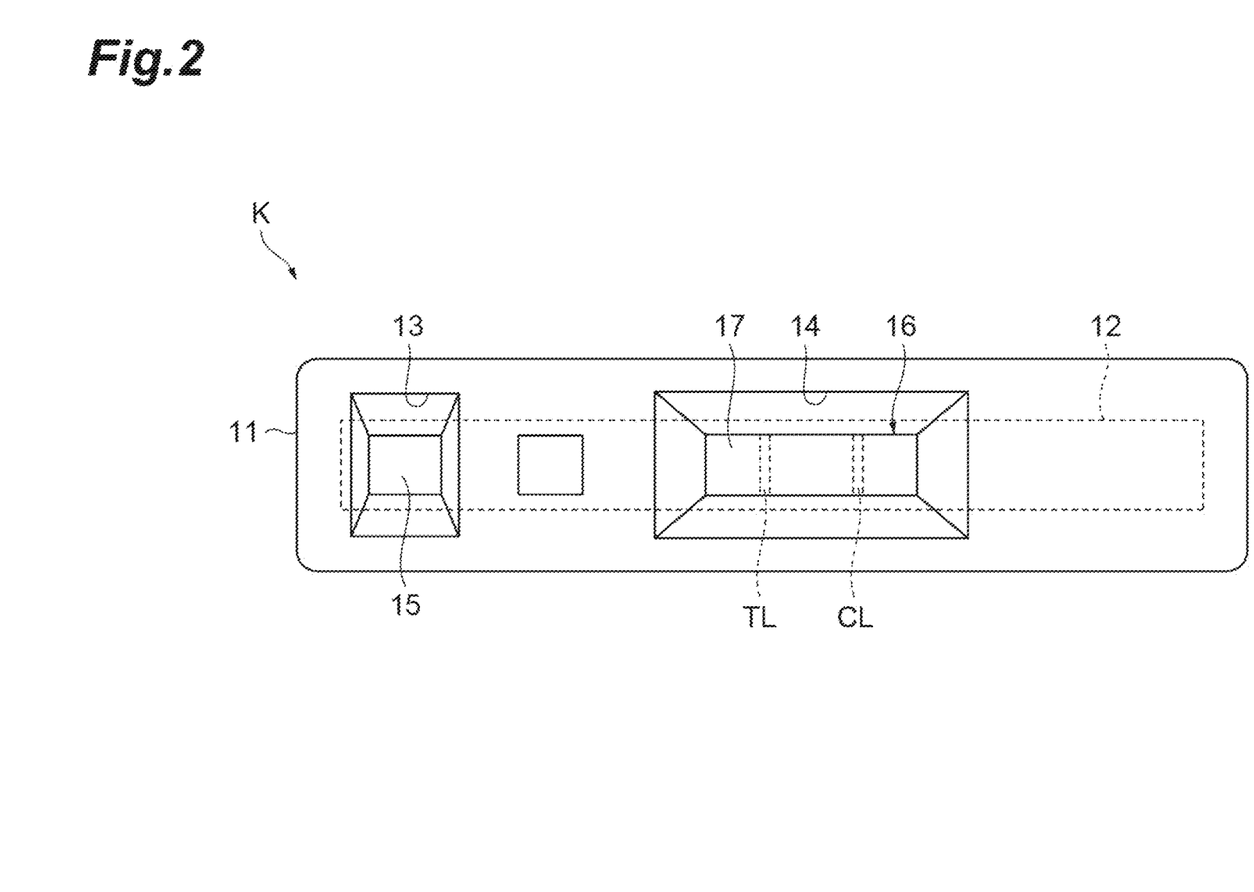
FIG. 2 is a plan view showing a configuration of a lateral flow test strip.

The lateral flow test strip K includes, as shown in FIG. 2, a casing 11 which has a rectangular shape in the plan view and a test strip body 12 which is held inside the casing. The casing 11 is provided with a sample application window 13 which drops a sample to one end portion of the test strip body 12 and an observation window 14 which exposes the substantially center portion of the test strip body 12 along the long side thereof.

The test strip body 12 is formed in a rectangular shape by, for example, a nitrocellulose membrane or a filter paper. The test strip body 12 includes a sample application portion 15 which is provided at a position corresponding to the sample application window 13 and a detection area 16 which is provided at a position corresponding to the observation window 14. In the test strip body 12, the sample developing direction is the direction from the sample application portion 15 to the detection area 16.

The detection area 16 is provided with the test line TL for determining the test result and a control line CL for determining whether or not the test is performed effectively in order from the front side of the sample developing direction at a predetermined interval. Both the test line TL and the control line CL are provided in a band shape in a direction intersecting the sample developing direction.

The sample is dropped from the sample application window 13 onto the sample application portion 15. The measurement target substance in the sample binds to a labeling substance such as gold colloid contained in a reagent and develops over time in the long side direction of the test strip body 12 together with the complex of the measurement target substance and the labeling substance in the sample and the unreacted labeling substance. When the sample reaches the detection area 16 as the sample is developed, the measurement target substance in the sample specifically reacts with the binding substance fixed to the test line TL and the control line CL and a line-shaped pattern (coloration line) colored by the labeling substance is formed. The coloration line can be observed through the observation window 14.

The reaction of the reagent proceeds over time after the sample is dropped onto the lateral flow test strip K. The reagent reaction usually continues to proceed unless the sample flowing with the reagent dries and sticks to the lateral flow test strip K. Thus, the coloration of the test line TL changes with time.

The optical head 2 includes, as shown in FIG. 1, a light emitting element 21, a light detection element 22, a luminous flux shaping member 23, and a lens 24. As the light emitting element 21, for example, a semiconductor light emitting element called a light emitting diode (LED) is used. As the light detection element 22, for example, a semiconductor light detection element called a silicon (Si) photodiode is used. The light emitting element 21 emits measurement light toward the test strip body 12. The optical axis of the light emitting element 21 is substantially perpendicular to the surface of the lateral flow test strip K. The light detection element 22 outputs an output signal corresponding to the intensity of the reflection light from the test strip body 12 to the determination unit 4. The optical axis of the light detection element 22 is inclined with respect to the optical axis of the light emitting element 21.

The luminous flux shaping member 23 is a plate-shaped member that shapes measurement light emitted from the light emitting element 21. A slit 23a extending in the same direction as those of the test line TL and the control line CL is provided at the center portion of the luminous flux shaping member 23. When the measurement light emitted from the light emitting element 21 passes through the slit 23a, the measurement light is shaped to have a band-shaped luminous flux cross-section extending in the same direction as those of the test line TL and the control line CL. Further, the lens 24 is disposed on the optical axis of the measurement light emitted from the light emitting element 21. The lens 24 forms an image of the measurement light having passed through the luminous flux shaping member 23 on the test strip body 12.

The control unit 3 is a part that controls the drive of the placement plate by the drive mechanism, controls the on/off state of the measurement light by the light emitting element 21, and processes the output signal of the light detection element 22. The control unit 3 drives the placement plate in the long side direction of the lateral flow test strip K with respect to the optical head 2. Accordingly, the detection area 16 of the lateral flow test strip K is scanned by the measurement light. The time required for one scan is sufficiently shorter than the measurement interval in the interval measurement described later.

The determination unit 4 is a part that makes a determination on the sample from the reaction between the measurement target substance in the sample and the binding substance. The determination unit 4 acquires the reflection light intensity on the basis of the output signal from the light detection element 22 and calculates the absorbance measurement value from the reflection light intensity. The determination unit 4 determines whether or not the sample held by the lateral flow test strip K is positive or negative on the basis of the comparison between the measurement value and the first threshold value set in advance. The determination unit 4 outputs information indicating a determination result to the display unit 5 and the display unit 5 displays the determination result on the basis of the information received from the determination unit 4.

Figure 3:
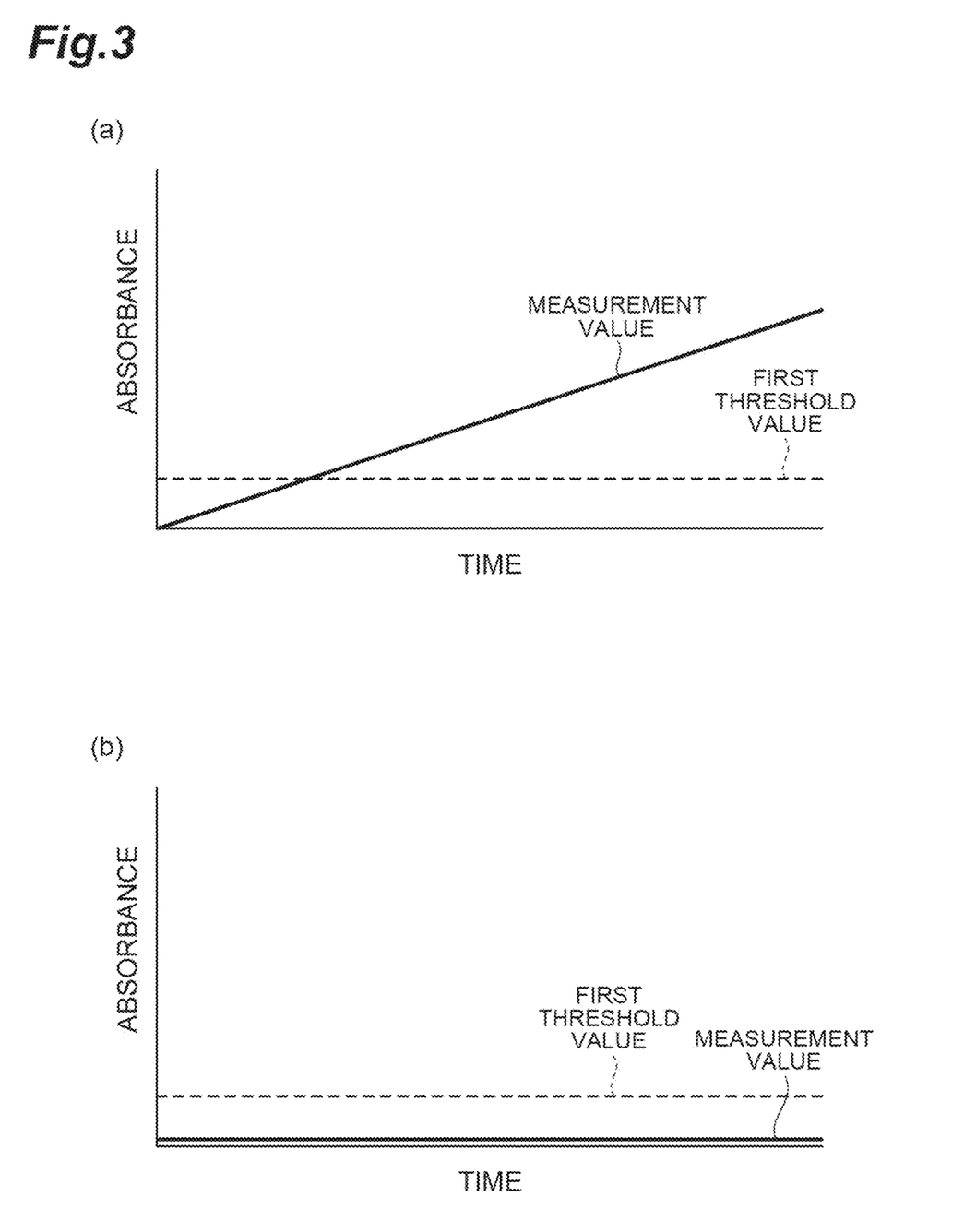
FIG. 3 is a schematic diagram showing a sample determination example when no foreign substance adheres to a detection area.

FIG. 3 is a schematic diagram showing an example of a behavior of the measurement value. In the same drawing, the horizontal axis indicates the time, the vertical axis indicates the measurement value (absorbance), and the first threshold value is indicated by the dashed line. Here, the first threshold value used to determine whether or not the sample is positive or negative is constant over the entire measurement period. When the sample is positive, for example, as shown in FIG. 3(a), the measurement value gradually increases as the measurement period elapses and the measurement value exceeds the first threshold value at any point from the start to the end of measurement. On the other hand, when the sample is negative, for example, as shown in FIG. 3(b), the measurement value does not increase as the measurement period elapses and the measurement value becomes the first threshold value or less over the entire measurement period.

Incidentally, in the inspection using the optical measurement device 1, the adhesion of the foreign substance to the detection area 16 of the lateral flow test strip K becomes a problem. As such a foreign substance, for example, powder of a constituent substance of the lateral flow test strip K is assumed. If such a foreign substance is transparent or white, it may be difficult to visually determine the presence or absence of adhesion. When the coloration state of the test line is optically read by using the lateral flow test strip K to which the foreign substance adheres, it is conceivable that the measurement value exceeds the first threshold value caused by the adhesion of the foreign substance and an originally negative sample is determined as positive.

Figure 4:
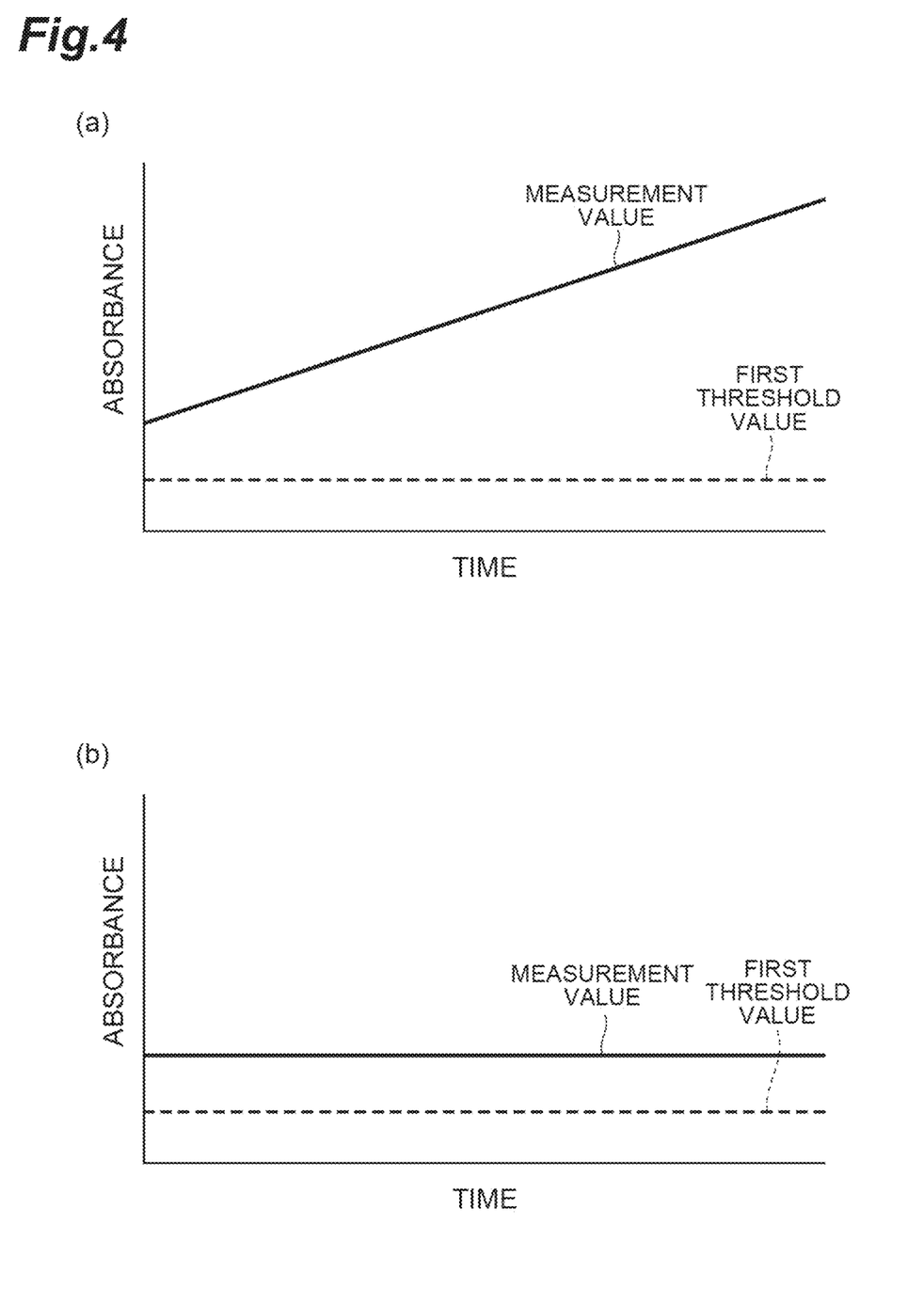
FIG. 4 is a schematic diagram showing a sample determination example when a foreign substance adheres to the detection area.

When the foreign substance adheres to the detection area 16 of the lateral flow test strip K, the measurement value caused by the adhesion of the foreign substance tends to have a constant value over the entire measurement period. Therefore, the measurement value may be a value obtained by adding the value caused by the adhesion of the foreign substance to the value caused by the reactivity between the measurement target substance in the sample and the binding substance. When the foreign substance adheres to the detection area 16 of the lateral flow test strip K and the sample is positive, for example, as shown in FIG. 4(*a*), the measurement value exceeds the first threshold value at the measurement start time point and the measurement value gradually increases as the measurement period elapses. In this case, since the measurement value exceeds the first threshold value over the entire measurement period, the determination unit 4 determines that the sample is positive. Thus, the adhesion of the foreign substance does not affect the sample determination result by the determination unit 4.

On the other hand, when the foreign substance adheres to the detection area 16 of the lateral flow test strip K and the sample is negative, for example, as shown in FIG. 4(*b*), the measurement value becomes a constant value exceeding the first threshold value over the entire measurement period. In this case, since the measurement value exceeds the first threshold value over the entire measurement period, the determination unit 4 determines that the sample is positive despite the fact that the sample is originally negative. Thus, the adhesion of the foreign substance affects the sample determination result by the determination unit 4.

On the other hand, the determination unit 4 of the optical measurement device 1 calculates the difference value between the initial measurement value and the latter measurement value when the measurement value exceeds the first threshold value. The determination unit 4 holds the second threshold value set in advance for the difference value. The determination unit 4 determines that the sample is positive when the difference value exceeds the second threshold value set in advance. The determination unit 4 determines that the sample is negative even when the measurement value exceeds the first threshold value when the difference value is the second threshold value or less.

The determination unit 4 may be configured to calculate the difference value when the measurement value exceeds the first threshold value at the reaction completion time point of the lateral flow test strip K or may be configured to calculate the difference value at a time point at which the measurement value exceeds the first threshold value (measurement times). In the description below, an embodiment is shown in which the determination unit 4 calculates the difference value when the measurement value exceeds the first threshold value at the reaction completion time point of the lateral flow test strip K.

Figure 5:
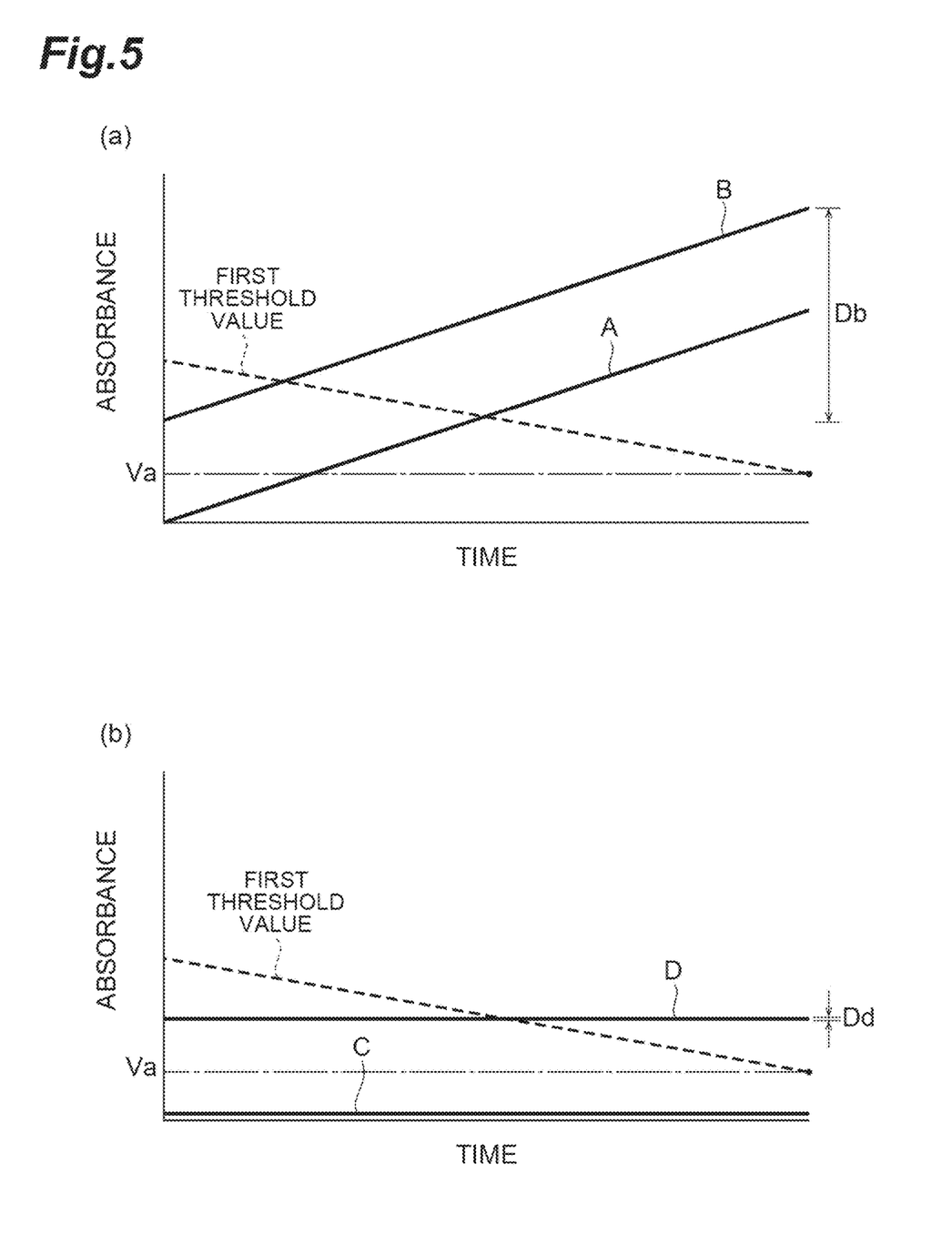
FIG. 5 is a schematic diagram showing a sample determination example of this embodiment.

FIG. 5 is a schematic diagram showing a sample determination example of this embodiment. In the example of the same drawing, similarly to FIGS. 3 and 4, the horizontal axis indicates the time, the vertical axis indicates the measurement value (absorbance), and the first threshold value is indicated by the dashed line. In the embodiment of FIG. 5, the first threshold value used to determine whether or not the sample is positive or negative is set to gradually decrease as the measurement period elapses. In this case, the determination unit 4 calculates the difference value when the measurement value exceeds the first threshold value and the initial measurement value exceeds the first threshold value at the latter measurement. Here, the initial measurement value is set as the measurement value at the measurement start time point and the latter measurement value is set as the measurement value at the reaction completion time point. The reaction completion time point is, for example, a time point at which a predetermined time for determining negative elapses. Further, the first threshold value at the latter measurement is set as the first threshold value (Va) at the measurement end time point.

The graph A of FIG. 5(*a*) shows a behavior of the measurement value when the foreign substance does not adhere to the detection area 16 of the lateral flow test strip K and the sample is positive. In the graph A, the measurement value is the first threshold value or less at the initial measurement and the measurement value exceeds the first threshold value at the latter measurement. Further, in the graph A, the initial measurement value is the first threshold value Va or less at the measurement end time. Thus, the determination unit 4 does not calculate the difference value and determines that the sample is positive.

The graph B of FIG. 5(*a*) shows a behavior of the measurement value when the foreign substance adheres to the detection area 16 of the lateral flow test strip K and the sample is positive. In the graph B, the measurement value is the first threshold value or less at the initial measurement, but the measurement value exceeds the first threshold value at the latter measurement. Further, in the graph B, the initial measurement value exceeds the first threshold value Va at the latter measurement. Therefore, the determination unit 4 calculates a difference value Db between the initial measurement value and the latter measurement value. In the graph B, since the difference value is sufficiently larger than the second threshold value (not shown), the determination unit 4 determines that the sample is positive.

The graph C of FIG. 5(*b*) shows a behavior of the measurement value when the foreign substance does not adhere to the detection area 16 of the lateral flow test strip K and the sample is negative. In the graph C, the measurement value is the first threshold value or less over the entire measurement period. Thus, the determination unit 4 determines that the sample is negative.

The graph D of FIG. 5(*b*) shows a behavior of the measurement value when the foreign substance adheres to the detection area 16 of the lateral flow test strip K and the sample is negative. In the graph D, the measurement value is the first threshold value or less at the initial measurement, but the measurement value exceeds the first threshold value at the latter measurement. Further, in the graph D, the initial measurement value exceeds the first threshold value Va at the latter measurement. Therefore, the determination unit 4 calculates a difference value Dd between the initial measurement value and the latter measurement value. In the graph D, since the difference value is sufficiently smaller than the second threshold value (not shown), the determination unit 4 determines that the sample is negative.

Next, the operation of the optical measurement device 1 will be described.

Figure 6:
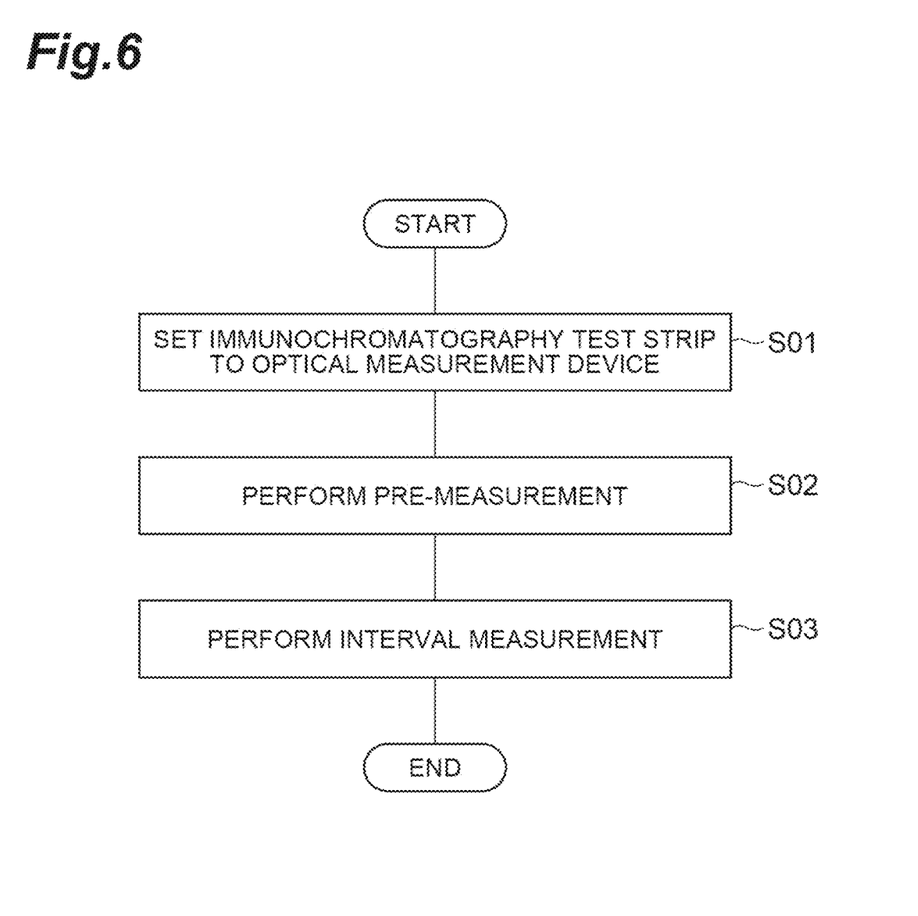
FIG. 6 is a flowchart showing an overall operation of the optical measurement device.

FIG. 6 is a flowchart showing an overall operation of the optical measurement device. As shown in the same drawing, the measurement step by the optical measurement device 1 includes a pre-measurement and an interval measurement. First, the lateral flow test strip K is set to the placement plate of the optical measurement device 1 (step S01). A measurer drops a sample onto the sample application window 13 of the lateral flow test strip K, for example, immediately before the placement on the placement plate. When a start operation (an operation of pressing a start button or the like) is input after the lateral flow test strip K is placed on the placement plate, the measurement of the lateral flow test strip K is started and the pre-measurement is performed (step S02).

In the pre-measurement, in order to check the reaction of the lateral flow test strip K to the control line CL at the initial measurement, the coloration of the control line CL is determined by the comparison between the measurement value of the light obtained from the control line CL and the threshold value set in advance. Based on this determination, it is checked whether or not the lateral flow test strip K set on the placement plate is in an appropriate state for measurement.

After the pre-measurement is performed, the interval measurement is performed (step S03). The interval measurement is a measurement in which the light obtained from the test line TL is measured at predetermined time intervals. The interval measurement may be continued until the reaction completion time of the reagent in the lateral flow test strip K or may be ended at a time point at which a determination is made before the reaction completion time. The reaction completion time is set in advance for each lateral flow test strip K (the combination of the material of the test strip body 12 and the type of reagent). As an example, when the reaction completion time is ten minutes, the interval measurement is performed up to ten times at one minute interval. In this case, the tenth interval measurement is a regular measurement corresponding to the reaction completion time. At the reaction completion time point, it is determined whether or not the sample is positive or negative on the basis of the comparison between the measurement value of the light obtained from the test line TL and the threshold value set in advance.

Figure 7:
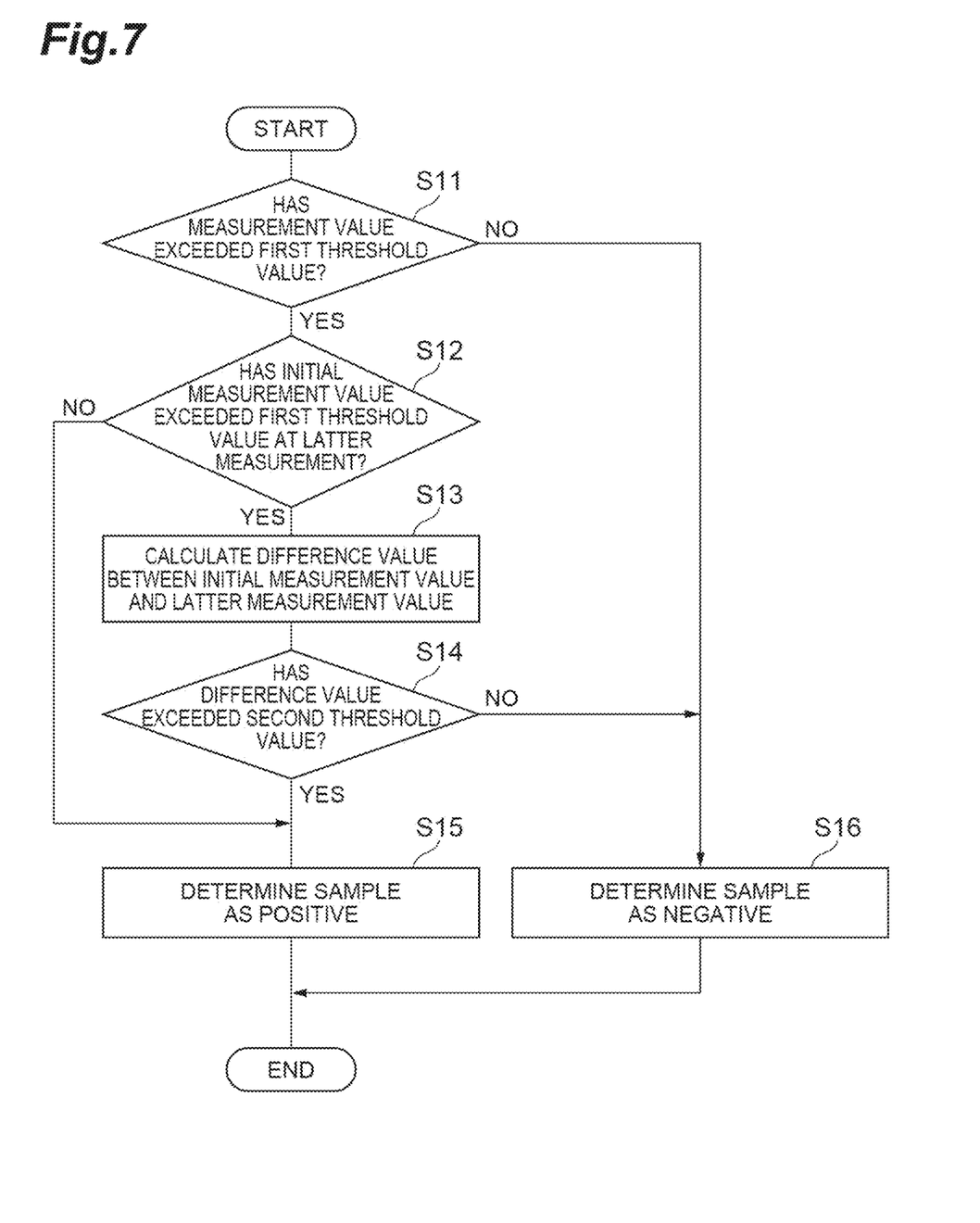
FIG. 7 is a flowchart showing a sample determination step.

FIG. 7 is a flowchart showing a sample determination step. In this embodiment, the sample determination step is performed after the reaction of the lateral flow test strip K is completed. As shown in the same drawing, in the sample determination step, it is first determined whether or not the measurement value exceeds the first threshold value (step S11). The routine proceeds to step S16 and when the measurement value is the first threshold value or less, the sample is determined as negative. When the measurement value exceeds the first threshold value, it is determined whether or not the initial measurement value exceeds the first threshold value at the latter measurement (step S12). When the initial measurement value is the first threshold value or less at the latter measurement, the routine proceeds to step S15 and the sample is determined as positive.

When the initial measurement value exceeds the first threshold value at the latter measurement, the difference value between the initial measurement value and the latter measurement value is calculated (step S13). After the calculation of the difference value, it is determined whether or not the difference value exceeds the second threshold value (step S14). When the difference value exceeds the second threshold value, it is determined that the sample is positive (step S15). When the difference value is the second threshold value or less, it is determined that the sample is negative (step S16).

As described above, in the optical measurement device 1, it is determined whether or not the sample held by the lateral flow test strip K is negative or positive on the basis of the comparison between the measurement value of the light obtained from the detection area 16 by the emission of the measurement light and the first threshold value set in advance. In this optical measurement device 1, the difference value between the initial measurement value and the latter measurement value is calculated when the measurement value exceeds the first threshold value. It is possible to distinguish whether or not the measurement value exceeding the first threshold value is caused by the adhesion of the foreign substance by comparing the difference value with the second threshold value. Thus, it is possible to ensure the sample determination accuracy even when the foreign substance adheres to the lateral flow test strip K.

In this embodiment, the first threshold value is set to gradually decrease as the measurement period elapses and the determination unit 4 calculates the difference value when the measurement value exceeds the first threshold value and the initial measurement value exceeds the first threshold value at the latter measurement. It is possible to improve the sample determination accuracy by setting the first threshold value to gradually decrease as the measurement period elapses. For example, it is possible to prevent the sample from being determined as positive by mistake when the coloration of the test line TL is temporarily increased due to the influence of the labeling substance unrelated to the test line TL (the labeling substance unrelated to the reaction related to the coloration of the test line TL) immediately after the sample is dropped. Further, it is possible to accurately distinguish whether or not the measurement value exceeding the first threshold value is caused by the adhesion of the foreign substance even when the first threshold value is set to gradually decrease as the measurement period elapses by comparing the initial measurement value with the first threshold value at the latter measurement.

Further, in this embodiment, the determination unit 4 calculates the difference value when the measurement value exceeds the first threshold value at the reaction completion time point of the lateral flow test strip K. In this way, it is possible to more accurately distinguish whether or not the measurement value exceeding the first threshold value is caused by the adhesion of the foreign substance by calculating the difference value when the measurement value exceeds the first threshold value after the reaction of the lateral flow test strip K is completed.

The present disclosure is not limited to the above-described embodiment. For example, in the above-described embodiment, the first threshold value is set to gradually decrease as the measurement period elapses, but the threshold value may be set to a constant value over the entire measurement period. Further, in the above-described embodiment, the lateral flow test strip K provided with one test line TL is illustrated, but a plurality of the test lines TL may be provided in the lateral flow test strip K. Further, in the above-described embodiment, both the measurement step and the determination step are performed by the optical measurement device 1. However, the optical measurement device may perform only the measurement step and the measurer may perform the determination step on the basis of the acquired measurement value.

Further, in the above-described embodiment, the absorbance calculated from the reflection light intensity of the measurement light is the measurement value, but as the measurement value, any other measurement value may be used as long as the measurement value is obtained on the basis of the light obtained from the detection area 16 by the emission of the measurement light. For example, an embodiment may be used in which the intensity of fluorescence excited by the emission of measurement light is used as a measurement value.

REFERENCE SIGNS LIST

1: optical measurement device, 2: optical head (measurement unit), 3: control unit (measurement unit), 4: determination unit, 16: detection area, K: lateral flow test strip.

The invention claimed is:

1. An optical measurement device comprising:
a measurement unit comprising a light-emitting element configured to emit measurement light to a single detection line of a lateral flow test strip and a light-receiving element configured to receive light obtained from the single detection line by the emission of the measurement light for a predetermined period and to output an output signal in accordance with an intensity of the light; and a determination unit comprising a computer in communication with the light-receiving element and configured to determine whether or not a sample held in the lateral flow test strip is negative or positive on the basis of a comparison between a measurement value in the single detection line obtained by the measurement unit and a first threshold value set in advance for determining the sample, wherein the determination unit determines an initial measurement value based on a first output signal at a first time, and a latter measurement value based on a second output signal at a second time after the first time, determines whether the measurement value exceeds the first threshold value;

calculates a difference value between an initial measurement value at a first time in the single detection line and a latter measurement value at a second time after the first time in the single detection line when the measurement value in the single detection line exceeds the first threshold value after the sample is held by the lateral flow test strip, determines whether the difference value exceeds a second threshold value, determines that the sample is positive when the difference value exceeds a second threshold value set in advance, and determines that the sample is negative when the difference value is the second threshold value or less.

2. The optical measurement device according to claim 1, wherein the first threshold value is set to gradually decrease as a measurement period elapses, and
wherein the determination unit calculates the difference value when the measurement value exceeds the first threshold value and the initial measurement value exceeds the first threshold value at the time of a latter measurement.

3. The optical measurement device according to claim 1, wherein the determination unit calculates the difference value when the measurement value exceeds the first threshold value at a reaction completion time point of the lateral flow test strip.

4. An optical measurement method comprising:
emitting measurement light from a light-emitting element to a single detection line of a lateral flow test strip and measuring receiving light obtained from the single detection line by the emission of the measurement light for a predetermined period with a light-receiving element configured to output an output signal in accordance with an intensity of the light; and determining with a computer in communication with the light-receiving element whether or not a sample held by the lateral flow test strip is negative or positive on the basis of a comparison between a measurement value in the single detection line obtained by the measuring and a first threshold value set in advance for determining the sample, wherein the determining step comprises:

determining an initial measurement value based on a first output signal at a first time, and a latter measurement value based on a second output signal at a second time after the first time, determining whether the measurement value exceeds the first threshold value;

calculating a difference value between an initial measurement value at a first time in the single detection line and a latter measurement value at a second time after the first time in the single detection line when the measurement value in the single detection line exceeds the first threshold value after the sample is held by the lateral flow test strip, determining whether the difference value exceeds a second threshold value, determining that the sample is positive when the difference value exceeds a second threshold value set in advance, and determining that the sample is negative when the difference value is the second threshold value or less.

5. The optical measurement method according to claim 4, wherein the first threshold value is set to gradually decrease as a measurement period elapses, and
wherein the determining step comprises calculating the difference value when the measurement value exceeds the first threshold value and the initial measurement value exceeds the first threshold value at the time of the latter measurement.

6. The optical measurement method according to claim 4, wherein the determining step comprises calculating the difference value when the measurement value exceeds the first threshold value at a reaction completion time point of the lateral flow test strip.

* * * * *